United States Patent [19]

Scott

[11] Patent Number: 5,096,291

[45] Date of Patent: Mar. 17, 1992

[54] INSPECTION SYSTEMS HAVING NUTATING MOTION

[75] Inventor: Daniel H. Scott, Northridge, Calif.

[73] Assignee: Irvine Optical Corporation, Burbank, Calif.

[21] Appl. No.: 523,984

[22] Filed: May 16, 1990

[51] Int. Cl.$^5$ .............................................. G01N 21/88
[52] U.S. Cl. ................................... 356/237; 356/426
[58] Field of Search ................ 356/237, 426, 336; 250/572

[56] References Cited

U.S. PATENT DOCUMENTS 4,893,932 1/1990 Knollenberg ................... 356/237 X Primary Examiner—Vincent P. McGraw
Attorney, Agent, or Firm—Merchant, Gould, Smith, Edell, Welter & Schmidt

[57] ABSTRACT

A positioning system is provided for positioning a part or element in different inclinations relative to a plane normal to a central axis, and for also rotating the part about the central axis. A holder supporting the part is freely pivotable about a point on the central axis. A central spindle on the axis is coupled to a concentric tiltable ring assembly that is controllable in two directions of freedom from an input device. The tilt and rotational motions of the ring assembly are translated to the part holder by a multi-element linkage mechanism having low friction bearings at each end and allowing a wide range of motion. The part may be a semiconductor wafer to be inspected for flaws on a holder comprising a vacuum chuck. Alternatively the tiltable, rotatable mechanism may be used to support an optical camera or viewing device, or a robotic mechanism, for operation within a wide field.

15 Claims, 7 Drawing Sheets

INSPECTION SYSTEMS HAVING NUTATING MOTION

BACKGROUND OF THE INVENTION

This invention relates to systems for providing selectable orbital and scanning motions about a central axis, and more particularly to systems for viewing defects on the surfaces of semiconductor wafers.

A number of applications exist in which it is desirable to control a member so that it can be arbitrarily tilted in any direction about a central axis, and also to rotate it in a true orbital motion in any inclination. Usually, it is desirable that there be a large possible angle of deviation from the central axis, and that the rotary control be operable separately or together with the tilting control. Examples of such systems are found in inspection applications, in compound motion mechanisms, and in systems in which a viewing device or optical unit is to be scanned or positioned within a large field of view.

An example of a critical inspection application is the so-called bright light inspection system for semiconductor applications. Semiconductor wafers, prior to deposition or etching, have highly polished surfaces which may include minute but visually observable defects such as finger marks, scratches, and lap lines. These can commonly be discerned by visual inspection at different angles under a strong light, properly oriented. In order for an inspector to see minute defects of different kinds, the wafer must be positionable at different angles and rotatable relative to the illumination. Different conditions of operation are best for searching for specific types of defects. For example, minute lines may only appear at certain angles, and particle matter may appear to luminesce briefly when moved through the light field. A range of tilt positions and a wide number of viewing perspectives should therefore be available along with the rotary motion.

In the inspection process, it is preferred to handle the wafers by an automatic transport mechanism which extracts them from one cassette and places them at the inspection position where they can be studied in different attitudes and motions. As determined by the inspector, an examined wafer may then be passed to a different cassette or returned to the original cassette, depending upon the wafer's acceptability, and the desired direction of flow.

There are a number of available wafer handling systems that incorporate a tilt and rotate feature, sometimes solely for purposes of bright light inspection and at other times to supplement an optical inspection utilizing a microscope. These systems are, however, restricted in their capability and not readily adjustable by the operator. Obviously, it is desirable to make it as convenient as possible for the operator to select and control the angle of inclination for inspection purposes. Moreover, the wafer should be arbitrarily tiltable along two orthogonally disposed directions (e.g. roll and pitch), and through substantial angles, such as ±45° relative to a plane normal to the axis of rotation. With such capability, the wafer can be tilted about one axis in a unidirectional scan, tilted concurrently about two axes to provide a warbling or wobbling motion, rotated in a fixed inclination about the central axis, or even tilted and rotated in a synchronized manner.

Prior art systems are limited in the fact that some can only be adjusted through a relatively small angle, some must be pre-set to a given angle, few provide a variety of control modes, and most are difficult and cumbersome to use, thus slowing the inspection process.

A reliable, precise mechanism for imparting such motions can be used in many other applications where comparable mechanical control is needed. A viewing device such as a CCD array can be directed, scanned or positioned anywhere within a wide field of view, or a robotic mechanism can be positioned in a confined space but be effective throughout a wide volume.

SUMMARY OF THE INVENTION

Systems and devices in accordance with the invention can separately or concurrently rotate a part or unit about a central axis while also selecting or changing its inclination relative to a reference point on the central axis. The part or unit is seated freely on a pivot ball mount to which is coupled one end of a central drive spindle that is disposed along and rotatable about the central axis. The central spindle is rotated by a drive system coupled to its opposite end, while an encompassing control ring is gimbal coupled to the spindle. The control ring thus is rotatable with the spindle but also tiltable with two degrees of freedom into arbitrary inclinations relative to a predetermined point on the central axis. An outer, non-rotating guidance ring is coupled by bearings about the control ring and engaged by a position control mechanism that inclines the ring assembly in either or both of two directions relative to a nominal central plane and about the predetermined point on the central axis. The rotational motion and the angle of inclination are translated to the part or unit by a system of control rods circumferentially spaced about and parallel to the central spindle. The ends of the control rods are coupled to the part holder and control ring respectively by low friction ball couplings which, together with the pivot ball on the center spindle, permit the inclination to be varied within a wide angle, such as an included angle of 90°. This system is therefore capable of receiving a part on the holder, tilting it in any direction about a pivot point through wide angles, and rotating it separately or concurrently with tilting.

Manual or automatic controls can be used in following a predetermined or arbitrary positioning sequence. The tilt mechanisms can be driven by stepper motors and the rotary drive by a variable speed motor, so that precise control with rapid adjustment can be readily achieved.

In accordance with other features of this arrangement, the part is a semiconductor wafer held on a vacuum chuck firmly during tilt and rotation. A vacuum line coupled to a carrier at the base of the spindle communicates suction to the vacuum chuck surface through a rotary seal via conduits extending through the center of the spindle, the pivot ball, and the vacuum chuck interior. The XY tilt mechanisms comprise separate compound pivot yokes coupled to the guidance ring and each driven by a lead screw controlled by a stepper motor supported on a gimballed actuator mount.

A feature of the invention is the provision of a low friction pivot ball having an interior vacuum conduit, and received within a chuck pivot socket so as to permit free tilting movement of the chuck and the attached wafer. Also satellite pivot balls and encompassing rings are used at each end of the control rods to provide low friction couplings in the tilt/rotate mechanism. The system thus obviates use of lubricants in the vicinity of the wafer that might degrade the stringent clean room conditions that have to be maintained.

In semiconductor inspection systems incorporating the tilt/rotation mechanism in accordance with the invention, wafers may be withdrawn from a supply cassette by a probe, and transported to the vacuum chuck. The tilt and rotate mechanism includes an elevator system for raising the mechanism and the chuck into a position for taking the wafer from the probe. In this position an operator may view light reflected off the wafer from an opposite bright light source. A tracking ball control is used by the operator to introduce single axis tilting or a compound wobbling motion, and a separate control is used for slow rotation. As a result of the inspection a decision is made as to the disposition of the wafer and the operator may enter commands on a keyboard as to the disposition of a wafer and also record data as to the inspection. Usually the choice is either to return the wafer to the supply cassette or cause it to be picked up by a separate probe and fed to a different cassette.

Although particularly suited for use in inspection of semiconductor wafers, systems and methods in accordance with the invention may be utilized for a wide range of other products which must be subjected to close examination. These include high precision parts such as those used in satellites, optical elements, and medical products, particularly for implantable devices. Further, the mechanism can serve as the positioning platform for a variety of scanning and controlled motion devices.

BRIEF DESCRIPTION OF THE DRAWINGS

A better understanding of the invention may be had by reference to the following description, taken in conjunction with the accompanying drawings, in which.

DETAILED DESCRIPTION OF THE INVENTION

Figure 1:
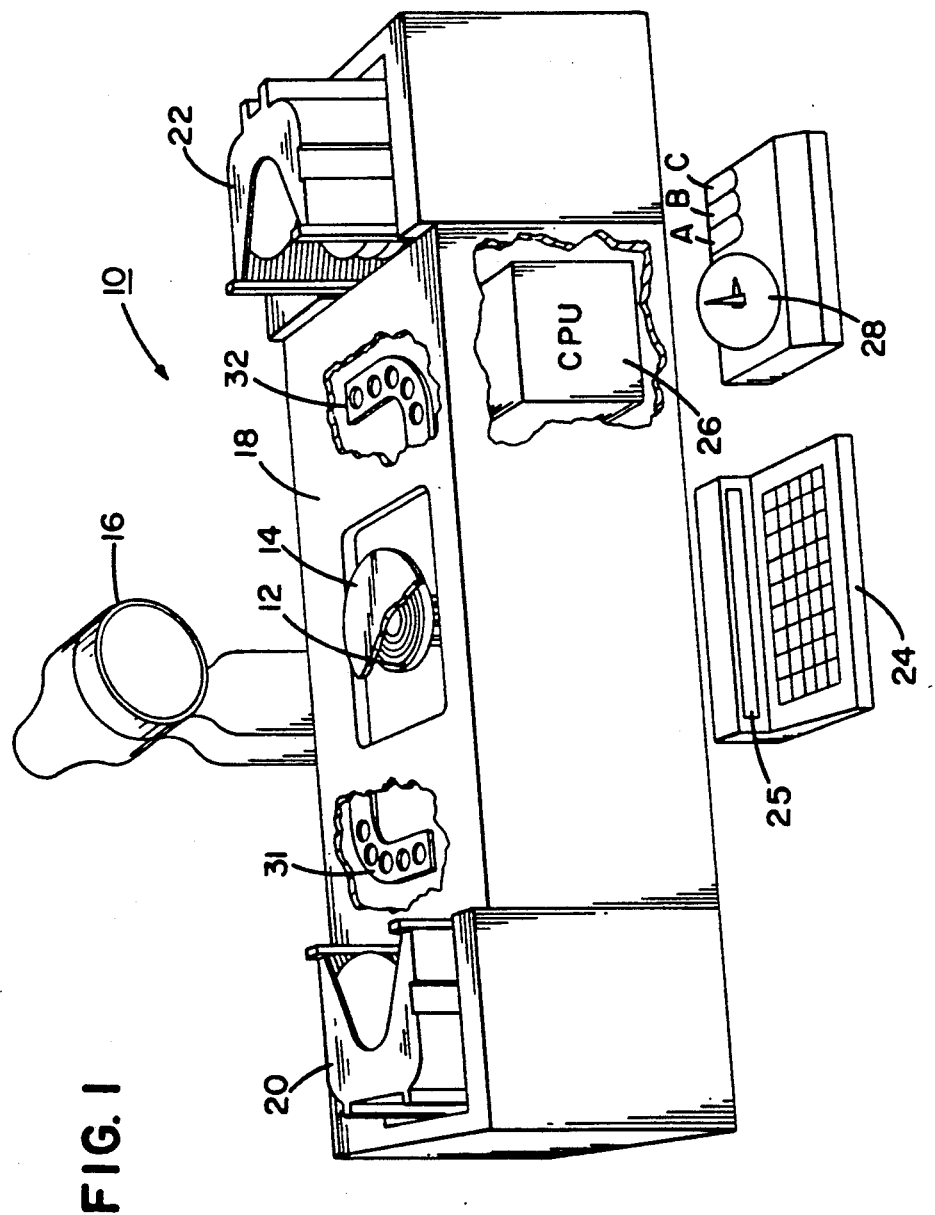
FIG. 1 is a perspective view of a system for bright light inspection of semiconductor wafers and other precision parts in accordance with the invention.

FIG. 1 depicts in general form one example of a system for providing controlled tilt and rotation through a wide angle. This is a bright light inspection system 10 including a vacuum chuck 12 disposed in a central position in front of an operator (not shown) who views light reflected off a semiconductor wafer 14 from a bright light source 16. The chuck 12 extends upwardly from a console 18 at what may be called the inspection position, to one side of which is disposed a supply cassette 20, while on the other side is disposed a take-up or secondary cassette 22. Elevator mechanisms that are used for lifting and lowering the cassettes so that individual wafers are made available are not shown or described in detail because they are well known. Either the supply cassette or the secondary cassette 20, 22 respectively may be used for receiving rejects, under control of an operator keyboard 24 with a line display 25, in conventional fashion. The operator also has a tracking ball type of mouse control 28 positioned for manual control of the tilting position, in X and Y, of the chuck 12 and the wafer 24. The mouse control 28 includes separate keys A, B and C for most used repetitive commands (e.g., reject, repeat cycle, accept). By X and Y are meant orthogonally disposed pitch and roll directions of motion relative to a central reference plane normal to the central or Z axis. The Z axis, about which the wafer 14 is to be rotated is in this instance vertical so that the reference plane is horizontal and the X and Y movements tilt the wafer 14 in either or both of the pitch and roll directions.

Within the console 18, a first probe 31 movable in the plane of the chuck 12 transports wafers between the supply cassette 20 and the chuck in conventional fashion, using suction to hold the wafer 14 in position. A second probe 32 is used between the chuck 12 and the secondary cassette 22. The line display 25 enables the operator to check commands as entered and to interact with a CPU 26, which is not described in detail as to data processing, recording and related functions are not of significance to the inventive feature. The CPU 26 operates in known fashion to control cassette elevation, cycling of the probes 31 and 32, and transfer of wafers 14 to and from the vacuum chuck 12 under control of the keyboard 24 and the mouse control 28.

Figure 2:
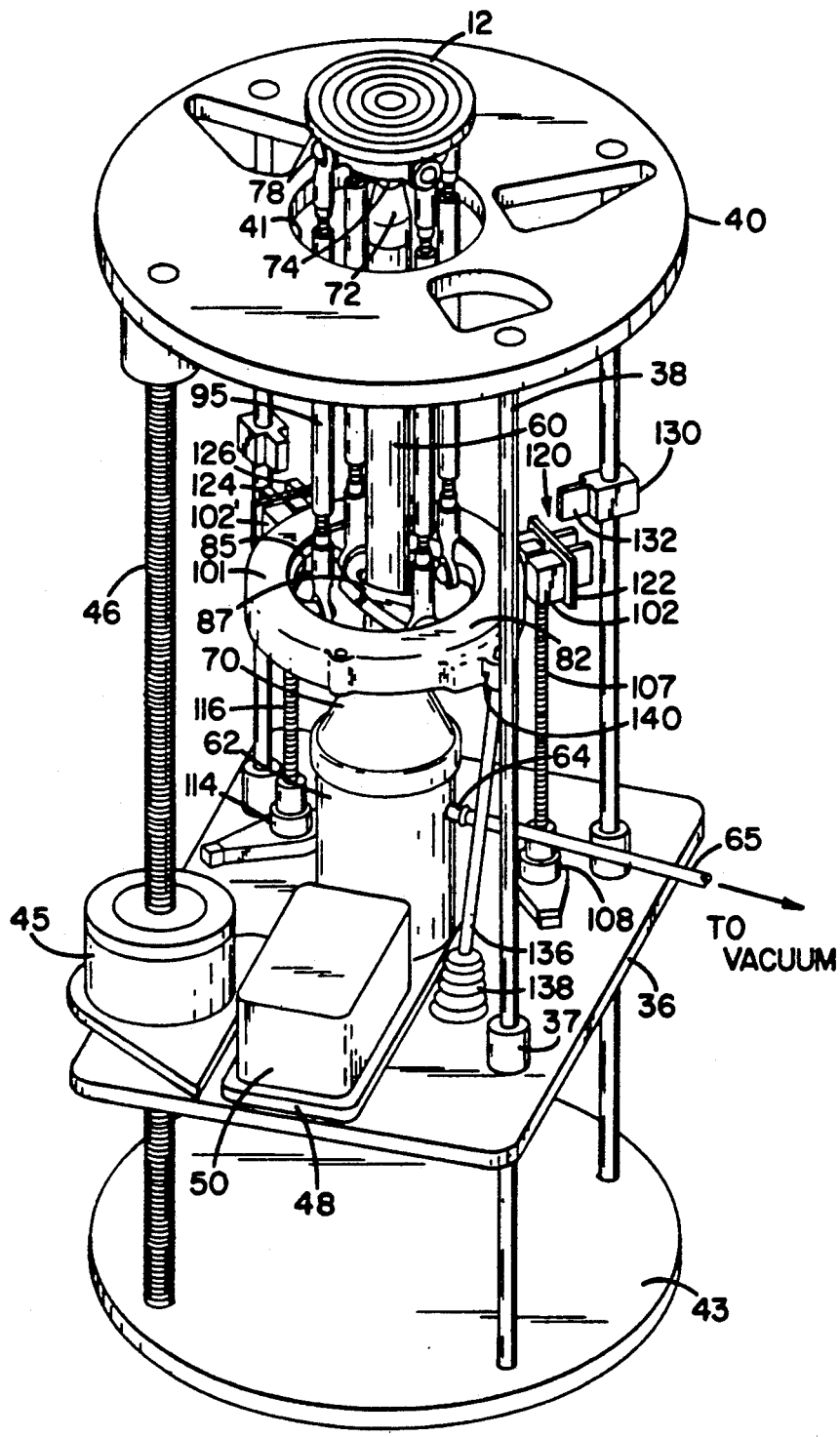
FIG. 2 is a perspective view of the principal elements of a system for tilting and rotating a part to be inspected.
Figure 3A:
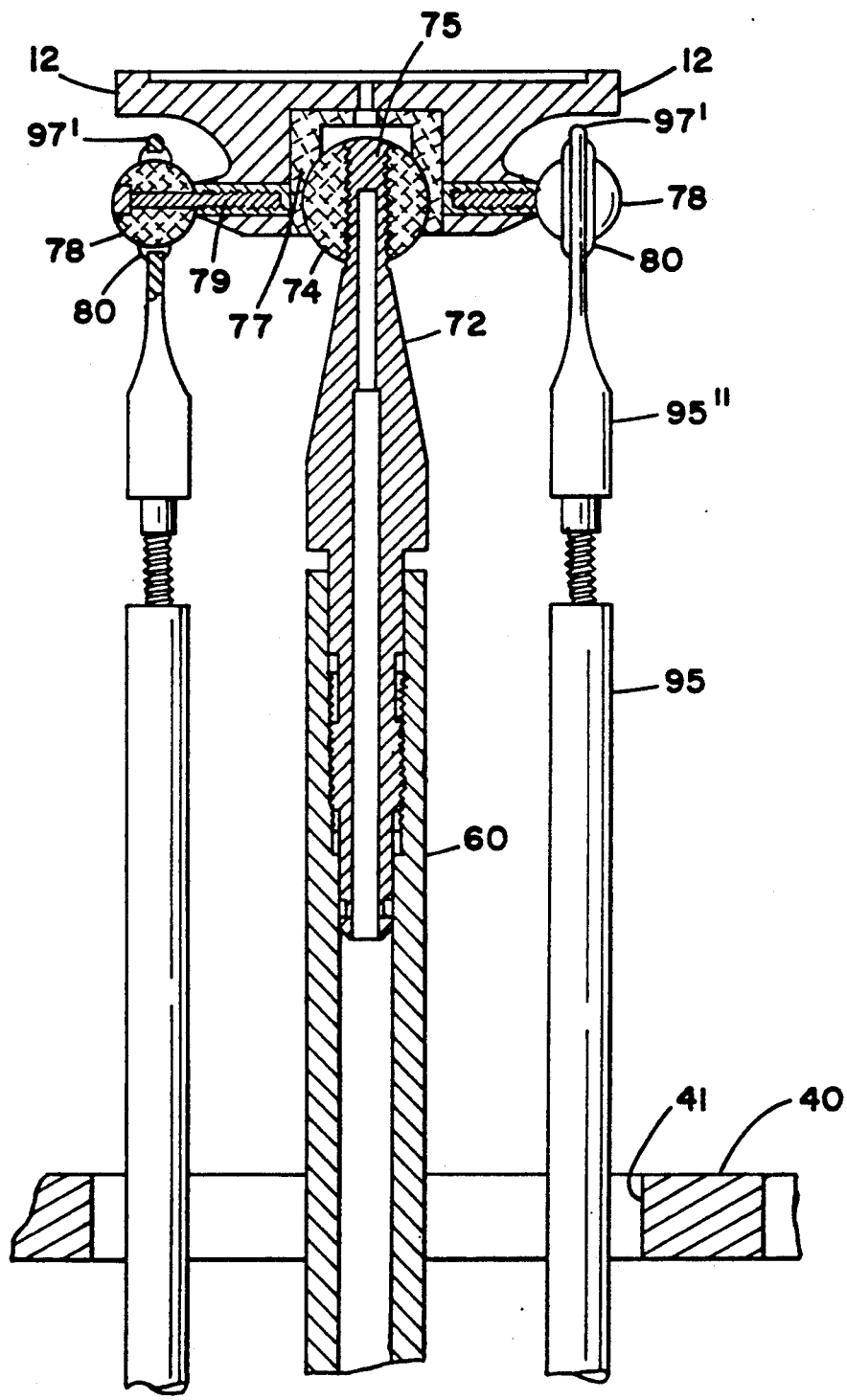
FIG. 3, comprising FIGS. 3A and 3B, which are to be viewed together, is a side sectional view of the device of FIG. 2.

The general arrangement of the tilt/rotate system is shown in FIGS. 2 and 3, to which reference is now made. Additional details of specific parts of the system are shown in figures referenced in detail hereafter. The tilt/rotate system is mounted so as to tilt and rotate the wafer 14 in X and Y around a point on the vertical central axis. The principal drive, support and control elements are enclosed within the console 18 of the system, except for the top protruding portion comprising the vacuum chuck 12 and its supporting elements, when extended to a raised inspection position. As seen in FIGS. 2 and 3, the drive units are mounted on a vertically movable Z axis drive plate 36 which includes slide bearings 37 receiving vertical guide rods 38. The upper ends of the rods 38 support a top plate 40 having a central aperture 41 concentric with the central axis. The guide rods 38 are seated in a base plate 43 and maintain the parallelism with the horizontal of the Z axis drive plate 36 as a Z axis motor 45 elevates or lowers the entire tilt/rotate mechanism via a large lead screw 46. Therefore, when the vacuum chuck 12 is lowered, the probes of FIG. 1 can transport wafers 14 to the central axis, and the vacuum chuck 12 can then be raised to slightly above the plane of the probes 31, 32 to an inspection position. Similarly, the chuck 12 can be lowered to deposit a wafer 14 on one of the probes 31, 32.

Figure 6:
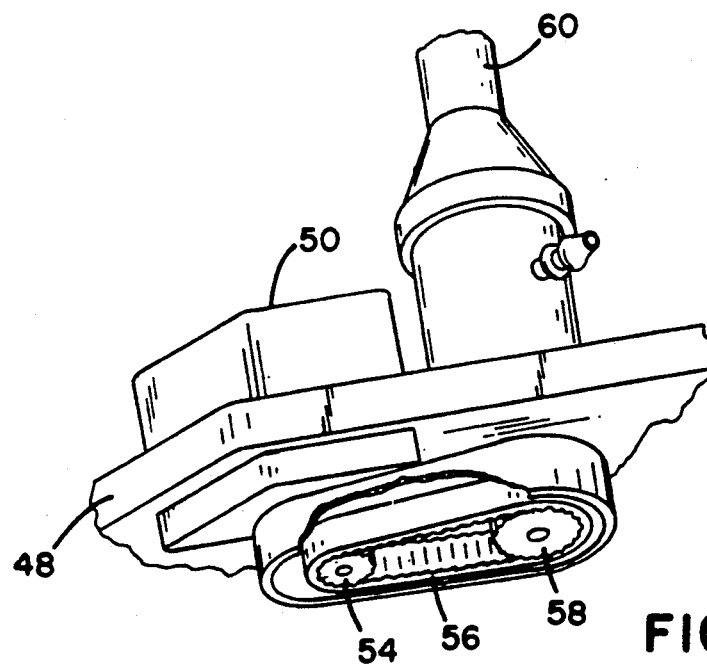
FIG. 6 is a fragmentary perspective view, partially broken away, of the drive mechanism for the center spindle.

A motor plate 48 on the upper side of the Z axis drive plate 36 holds a spindle drive motor 50, the shaft of which extends downwardly through the motor plate 48 to a drive gear 54 coupled by a drive belt 56 to a driven gear 58 coupled to the rotatable center spindle 60 (FIGS. 3 and 6).

As best seen in FIG. 3, the spindle 60 is mounted on ball bearings 61 in a stationary Z bearing carrier 62 on a spindle support 63. The Z bearing carrier 62 includes a vacuum line fitting 64 (FIG. 2) to which an external vacuum line 65 (FIG. 2 also) is attached. The interior of the Z bearing carrier 62 includes a vacuum feed bushing 66 which includes a hole 67 opening the vacuum line fitting 64 to a bore 68 in the spindle 60, while sealing out other air flow to prevent loss of suction.

The intermediate portion of the center spindle 60 includes a conical base 70 from which the principal upstanding portion of the spindle 60 extends. The center spindle 60 is hollow, communicating the vacuum line with an uppermost vertically adjustable tapered tip 72 coupled into a central pivot ball 74 of inert, very low friction, material such as "Teflon," best seen in FIG. 3A, that includes an aperture 75 in communication with the surface of the vacuum chuck 12. The pivot ball 74 is itself seated in mating fashion within a chuck pivot socket 77 of "Teflon" in the vacuum chuck 12.

Exterior to the chuck 12, attached at different equally spaced points on its periphery, are a number (here four) of satellite pivot balls 78 secured by threaded bolts 79. The satellite pivot balls 78 are essentially spherical and also of "Teflon", further being held within "Teflon" rings 80 of relatively small width which slide freely through considerable arcs on the balls 78, since the geometry provides clearance through wide angles without contact of abutting surfaces. With proper fabrication practices and with smooth exterior surfaces on the balls and the mating bodies in which they are seated, the chuck 12 moves very freely but without the sources of contamination a chemical lubricant would present in the vicinity of a wafer. To assure conformity of the Teflon balls and rings, and low friction operation, it has been found advantageous to heat the assembly to an elevated temperature and to suddenly cool it.

Figure 3B:
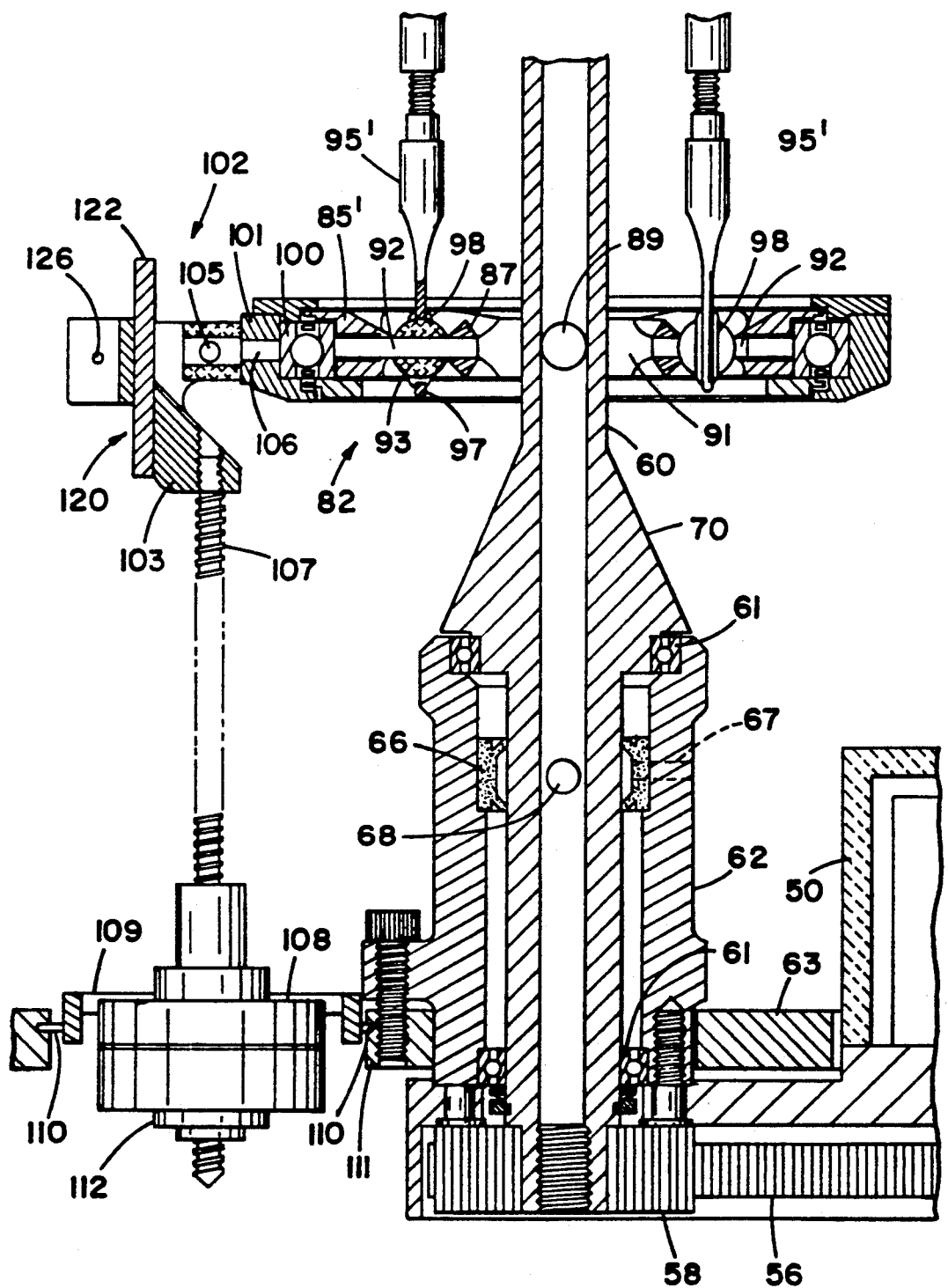
Figure 4:
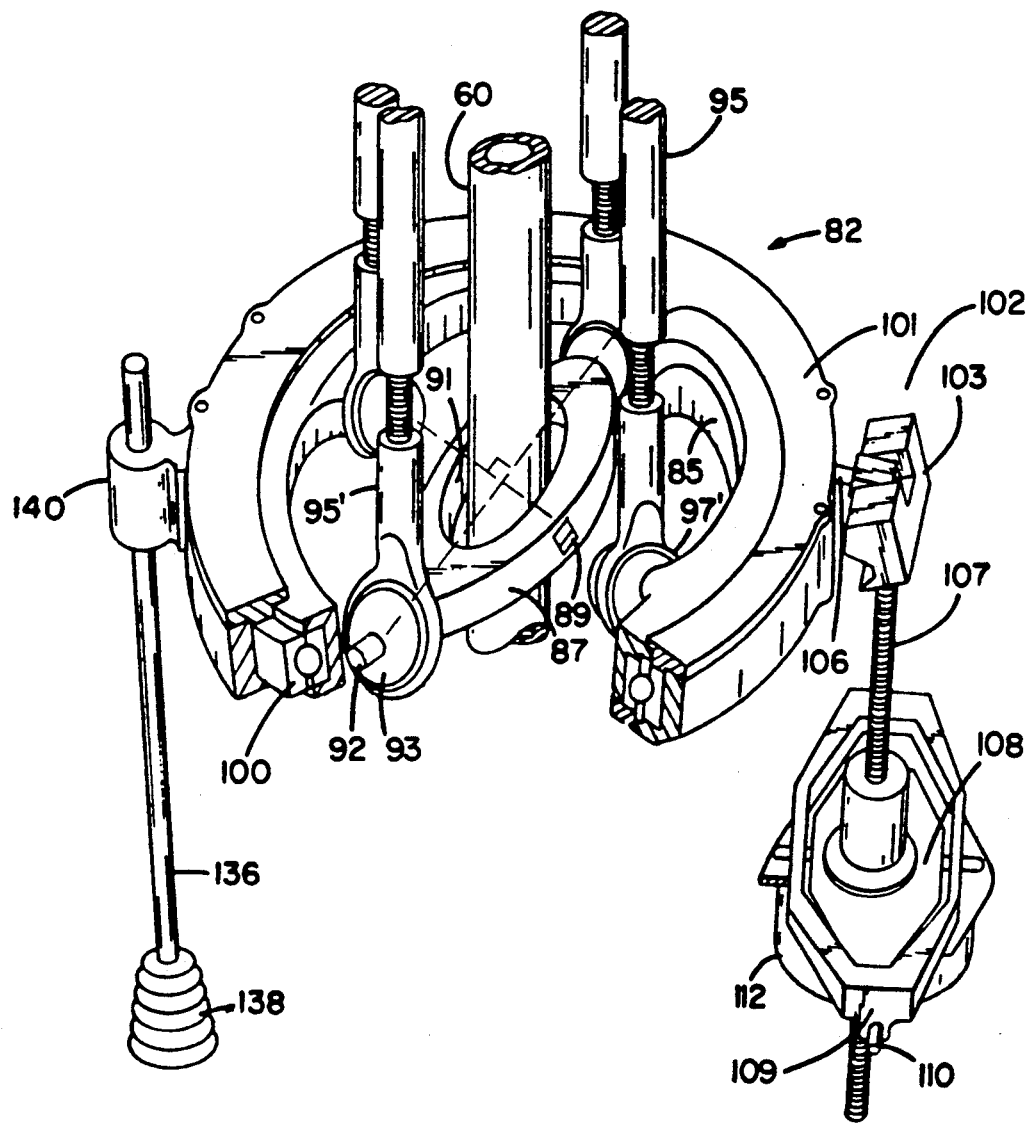
FIG. 4 is a fragmentary perspective view of a ring assembly and XY tilt mechanism utilized in the arrangement of FIGS. 1-3.

The tilting and rotating mechanism for providing a true orbital motion about the central axis includes a gimbal mounted ring assembly 82, seen best in FIGS. 2, 3 and 4. The ring assembly 82 comprises an inner control ring 85 disposed concentric with the central axis and adjacent the conical base 70 portion of the center spindle 60. The control ring 85 is coupled to the center spindle 60 by a drive gimbal 87 at a transverse pin 89, thus imparting rotation while allowing a first degree of tilt freedom. The gimbal 87 has a central bore 91 sized and shaped to permit tilting motion through more than ±45° without contact with the outer surface of the central shaft 60. Short shafts 92 couple the control ring 85 radially to the ends of the drive gimbal 87 in the direction orthogonal to the transverse pin 89. Full gimballing action, in a second degree of freedom, is provided by low friction (e.g. "Teflon") bearing spheres 93 on the shafts 92 between the drive gimbal 87 and the inner control ring 85. The bearing spheres 93 provide lower attachment points for circumferentially spaced, parallel control rods 95 that extend vertically up to satellite pivot balls 78 at the vacuum chuck 12 assembly. The lower ends of the control rods 95 taper to eyes 97 that contain narrow "Teflon" rings 98 which fit in mating relation about the bearing spheres 93. Here also a low friction coupling is provided that permits free tilting movement in any direction (within geometrical limits defined by clearance relative to adjacent units) of the control ring 85. Although only three control rods 95 need be used to define a plane, this is a matter of design choice, and four control rods provide better symmetry against torsional forces.

The upper ends of the control rods 95 also include eyes 97' holding the rings 80 that fit around the satellite pivot balls 78. Thus changes in inclination at the control ring 85 are coupled to the vacuum chuck 12 by the rods 95 to cause the vacuum chuck 12 to assume a like inclination. The control rods 95 also rotate the vacuum chuck 12 with the center spindle 60, when it is turned. Although the control rods 95 may be made as a single piece, they as shown here as comprising three-piece elements, with an end section 95' at the lower end and an end section 95" at the upper end, the center section being threaded into each of the end sections to permit adjustment of length. This allows adjustment of the control rod 95 lengths, but adequate adjustment is usually obtained by threading the upper end of the center spindle 60 up or down.

The XY positioning mechanism for tilting the control ring 85 functions about the two parallel axes that are in planes that intercept the central axis but are orthogonally disposed relative to each other, and determine X and Y tilting. The mechanism comprises a bearing ring 100 whose inner half is coupled to the outer perimeter of the control ring 85, and an outer guidance ring 101 that is stationary and coupled to the outer half of bearing ring 100. A compound pivot yoke 102, 102' is provided for each of the X and Y tilt axes. As seen in FIGS. 3 and 4 the compound pivot yokes 102, 102' each include an upper bracket 103 having a U-shaped head within which a short arm 104 is seated on a pivot 105. A finger 106 extends from the arm 104 and is coupled into the adjacent portion of the guidance ring 101, as best seen in FIGS. 3 and 4.

For X and Y control, a lead screw 107 seated rotatably in the upper bracket 103 at its upper end, is movable substantially vertically in a fixed element on an actuator mount 108, the actuator mount 108 being held in a gimbal 109 having two degrees of freedom. Pivot pins 110 at the ends of the gimbal 109 seat in blocks 111 on the spindle support 63. A stepper motor 112 is mounted on the underside of the actuator mount 108 to drive the lead screw 107 up and down, while pivoting on the gimbal 109 in the direction toward and away from the central axis to adjust for changes in the length of the lead screw 107 between the mount 108 and the upper bracket 103. The actuator mount 108 is gimballed to allow slight torsional displacements of the control rods 95 because their ends are not restrained in the circumferential direction except when a limit is reached. The compound pivot yokes 102, 102' thus allow for some side movement relative to the principal arc. The stepper motor 112 is of the type in which the lead screw 107 passes through the central axis, thus conserving space and simplifying the mechanism.

As best seen in FIG. 2, the second compound pivot yoke 102' is mounted on a different gimballed actuator mount 114 lying in the same horizontal plane as the first described yoke 102, but pivoting with change of lead screw 116 length about an axis that is in an orthogonally disposed plane relative to the central axis. Both XY drives thus principally move through an arc lying in a plane that intercepts the central axis, but accommodate some lateral movement relative to that plane as well.

Figure 5:
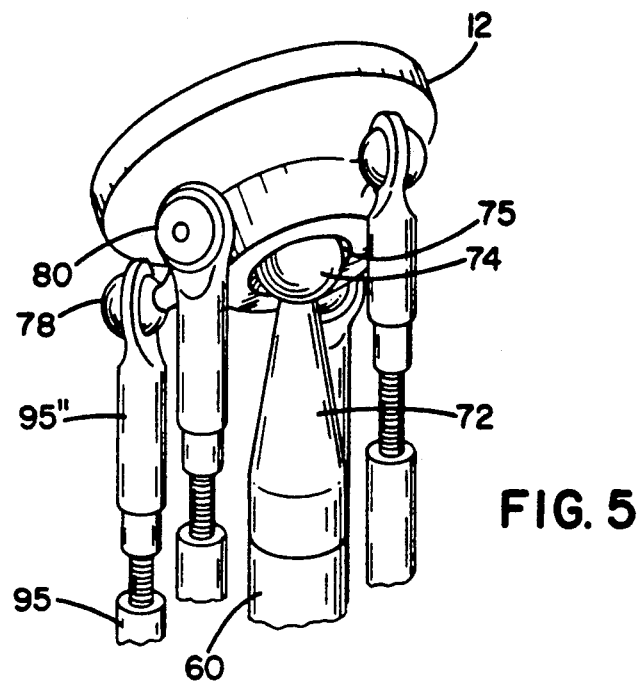
FIG. 5 is a fragmentary perspective view of a portion of the tilt/control mechanism, showing further details of the mechanism at the upper end of the center spindle.
Figure 7:
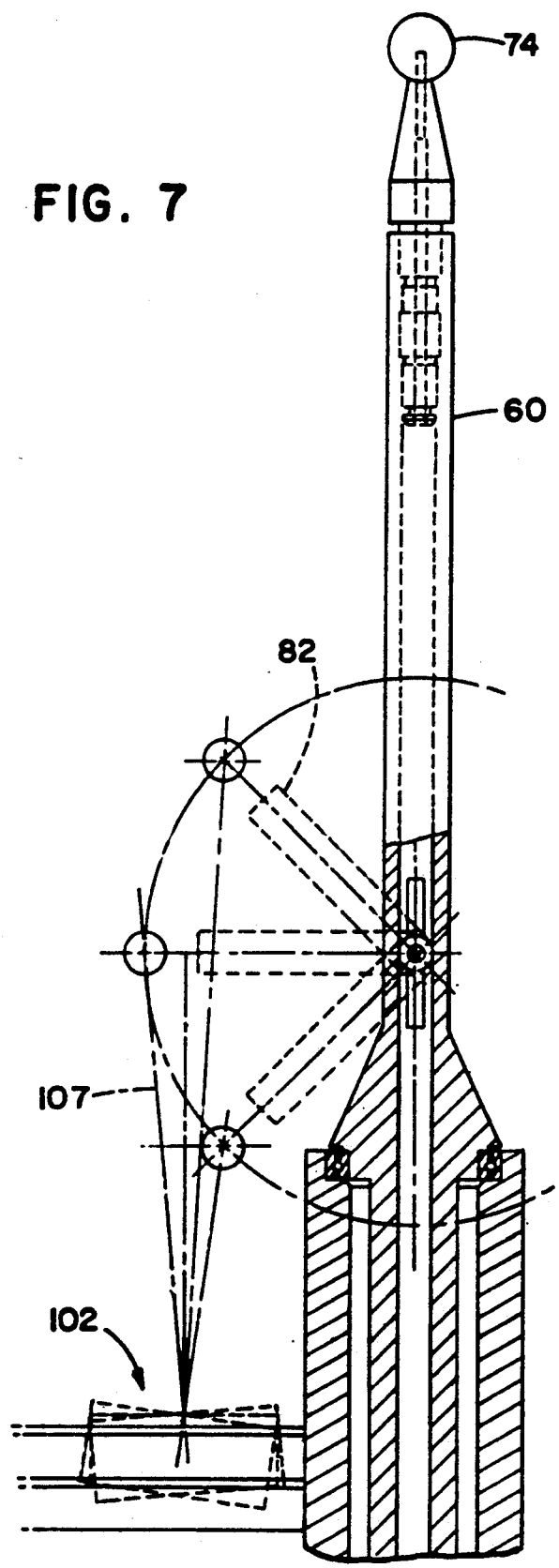
FIG. 7 is a side schematic view showing changes in position as the tilt mechanism is operated through a range of motion.

The side view of FIG. 7 diagrammatically illustrates the principal pivot action of one of these pivot yokes, as the ring assembly 82 is shifted between limit positions about the central pivot point, defining an instantaneous angle of anywhere between +45° to −45° relative to the horizontal reference plane. As also seen in FIG. 7, when the control ring 85 is tilted, the angle of the lead screw 107 (or 116) (diagrammatically illustrated only) relative to the vertical is changed correspondingly. At the same time, the gimballed ring assembly 82 tilt causes the control rods 95 to move radially inwardly toward the center spindle 60, where there is inclination relative to a horizontal reference plane normal to the control axis. The motion of a point on the gimballed control ring 85 is orbital when ring 85 is rotated in a given inclination. As seen in FIG. 5, this motion is translated by the control rods 95 and the satellite pivot balls 78 into an identical orientation and orbital rotation of the vacuum chuck 12. Angular play at the outset of angular motion in each direction is limited and does not affect the inspection process.

The suction on the underside of a wafer 14 on the vacuum chuck 12 is maintained during rotation. As seen in FIG. 3B, a vacuum is drawn on the Z bearing carrier 62 into the interior chamber within the vacuum feed bushing 66. The interior is sealed but coupled into the conduit extending vertically along the hollow center spindle 60, then to the central pivot ball 74, and to the surface of the vacuum chuck 12 in FIG. 3A.

The compound pivot yokes 102, 102' incline the ring assembly 82 at arbitrary angles, but it is desirable to limit the range of movement automatically, so as to preclude stressing the motor and mechanism. For this purpose, as seen in FIGS. 2 and 3B, an optical sensor 120 is mounted on the outer radial side of each bracket 103. The optical sensor 120 arrangement is alike for each of the pivot yokes and so only one sensor need be described. It includes a small circuit board 122 interconnected with the CPU 26 and with a light source element 124 and a light sensor element 126, the two elements 124 and 126 being spaced apart by a gap that is vertically aligned with and adjacent to one of the guide rods 38. A flag element 130 is selectably positionable in height on the rod 38, as by a set screw (not shown) and includes a tab 132 lying in the vertical plane which intercepts the gap between the source element 124 and sensor element 126. Thus, if the angle of inclination of the ring assembly 82 reaches the limit defined by the flag element 130 position, a signal is transmitted to the CPU 26 and the associated drive motor 112 is disabled from further movement in that direction by blocking further commands from the tracking ball mouse control 28.

Alternatively, the flag element 130 can be of the type in which a long strip having one or more sensor holes is positioned along the rod. The strip may occlude the sensor from the light source except when the light beam passes through the sensor hole, signaling the CPU 26 that the ring assembly 82 is at the limit position. An inverse sensor system, having a slot between limit positions, may also be used. In all arrangements both lower and upper limit positions may be sensed, this feature not being shown in detail for simplicity.

To stabilize the ring assembly 82 the guidance ring 101 is mechanically biased to the central reference plane position in which it is normal to the vertical central axis. This may be accomplished by a set of light tension springs (not shown) anchoring the guidance ring 101 to fixed parts of the structure so as to provide low force loads against both up and down movements. In the present example, however, a bar 136 is disposed in a generally vertical orientation between a spring 138 coupled to the Z axis drive plate 36 at one end, and a sleeve 140 pivotally coupled to the guidance ring 101 at the other end. The spring 138 is in a neutral position when the ring assembly 82 is centered, but functions in both tension and compression to provide a light opposing load to inclination of the assembly 82.

In the operation of the system of FIGS. 1–7, an operator seated in front of the console 18 uses the keyboard 24 and the CPU 26 to elevate or lower the supply cassette 20 to a selected level, then cause the first probe 31 to withdraw a wafer 14 from the selected position. The wafer 14 is shifted along a horizontal plane to above the lowered vacuum chuck 12, which is then raised and a suction applied. At contact with the vacuum chuck 12 the wafer 14 is transferred from the probe 31 by release of suction on the probe 31 and application of suction on the chuck 12, before or as it raises to the inspection plane. When the wafer 14 is in position the beam from the bright light 16 is reflected off the wafer 14 toward the operator, who can start the inspection process, in automatic or manual controlled sequences. When the inspection procedure is complete, the wafer can then be returned to the supply cassette 20 by the first probe 31 or passed on to the secondary cassette 22 by the second probe 32, depending on which of those cassettes is used for accepted and rejected wafers.

The inspection procedure can be manual, controlled solely by the operator, or completely automatic, under CPU 26 control, or a combination of both. In the automatic mode, by which higher throughput can usually be achieved, the selected wafer 14 is placed on the chuck 12, and various tilt and rotation subroutines are carried out. In the manual mode, the tilt and rotation ($\theta$) controls can be used in arbitrary fashion.

The operator, with training and experience, quickly becomes astute in using different angles and modes to look for different types of defects in the wafer 14 surface. To control tilt, the operator simply rotates the tracking ball on the mouse control 28 in the back/forth or right/left directions. To create a warbling motion he moves the tracking ball 28 in a circular motion. Such actions quickly become instinctive since the operator is immediately aware of the responsive change in position. In response, the stepper motors, e.g. 112, control the XY position with sufficient precision for close examination. Tilting can be carried out prior to or during rotation, as desired, so as to effect a scanning action using tilt alone or to scan using rotation. Consequently, if the wafer 14 is not clean, has lap marks or scratches, or other blemishes, the bright light illumination will show a significant flaw visibly at some point in the inspection process.

It should be appreciated that this tilt/rotate system can be utilized in a variety of applications and systems that require comparable compound motions through a wide range. As mentioned above, implantable medical devices, precision components for satellite installations, extremely high precision units, and other devices require very careful visual checking and can be inspected in a comparable manner. These can be placed on a tiltable, orbitally rotatable, holder of a type compatible for the part, by a conventional robotic or other pick and place mechanism, then inspected in comparable fashion. The same structure makes feasible automatic inspection systems, in which the pivot and rotational operations are controlled by a processor in programmed fashion, and the light reflected off the part being inspected is detected by a scanning mechanism or matrix and then analyzed in analog or digital circuitry. For example, the pivot position and angular position can be sequenced through a number of steps, and a digitized image can be derived at each step, with the images being analyzed in comparison to a number of standard images, and high amplitude and low amplitude excursions, relative to the standards, being used as indicators of likely fault conditions.

A TV camera or CCD matrix can be placed on a holder and both inclined and rotated through a wide angle, providing an extremely broad field of view. Remote control systems can employ this arrangement with benefit. Similarly a beam scanning device can be controlled in comparable fashion, or a robotic arm mounted on a tiltable, rotatable base in this manner, can cover an extremely wide working area from a focal region.

Although there have been described above various forms and modifications in accordance with the invention, it will be appreciated that the invention is not limited thereto but encompasses all modifications and exemplifications within the scope of the appended claims.

What is claimed is:

1. A system including a rotatable part holder concentrically disposed about a central axis for varying the angle of tilt of the part holder and a part thereon relative to a reference plane normal to the central axis while providing orbital motion about the central axis, the system comprising:
   part holder means including pivot ball means at the central axis;
   a central spindle disposed along and concentric with the central axis, a first end of the central spindle being coupled to the pivot ball means;
   means coupled to a second end of the central spindle for rotating the central spindle about the central axis;
   control ring means disposed about an intermediate position of the central spindle, and including gimbal means for maintaining the control ring means in a plane that intercepts a predetermined point on the central axis;
   means coupled to the control ring means for positioning the control ring means at a selectable angle of inclination variable in two directions relative to a plane parallel to the reference plane and intercepting the predetermined point; and
   means coupling the control ring means to the part holder for varying the inclination of the part holder in correspondence to that of the control ring means while also rotating the part holder about the central axis.

2. A system as set forth in claim 1 above, wherein the means coupling the control ring means to the part holder comprises a number of control rods substantially parallel to the central axis and low friction means separately coupling the ends of the control rods to the control ring means and part holder with two degrees of freedom.

3. A system as set forth in claim 2 above, wherein the low friction means comprise individual satellite balls coupled to the control ring means and part holder respectively at different circumferential positions and low friction rings coupled to the control rods and individually seated on the satellite balls.

4. A system as set forth in claim 3 above, wherein the means for positioning the control ring means comprises guidance ring means disposed about the control ring means, bearing ring means coupling the guidance ring means to the control ring means, and means engaging the guidance ring means at two different circumferential regions for tilting the guidance ring means in two different directions relative to the central axis.

5. A system as set forth in claim 4 above, wherein the gimbal means couples the control ring means to the central spindle, and the rotation of the central spindle imparts rotation to the control rods and the part holder.

6. A system as set forth in claim 1 above, wherein the means for positioning means comprises a pair of compound yoke means each including motor means, lead screw means driven thereby, and means coupling the lead screw means to the control ring means, the lead screw means being movable through an arc toward and away from the central axis within a given plane intersecting the central axis.

7. A system as set forth in claim 6 above, wherein the compound yoke means each comprises gimbal means supporting the motor means and lead screw means, and the arcs of the lead screw means moving in orthogonal planes that intersect the central axis.

8. The invention as set forth in claim 1 above, wherein the gimbal means has two degrees of freedom of motion relative to the reference plane normal to the central axis and the means for positioning comprises an outer ring and bearing means coupled to the control ring, extendable means including drive means disposed on the pivot axes and an elongated member coupled to the other ring for changing the pivot position of the outer ring and the control ring means in response to the extension or contraction of the extendable means.

9. A system for tilting and rotating a part on a part holder comprising:
   a central spindle coupled to the part holder and rotatable relative thereto about a central axis;
   ring assembly means disposed about the central spindle at a region spaced apart from the part holder, the ring assembly means including gimbal means coupled to the central spindle and tiltable in orthogonally disposed directions relative to the central axis, and outer nonrotating means tiltable therewith;
   positioning means coupled to the non-rotating means of the ring assembly means and for controlling the tilt thereof; and
   transmission means coupling the ring assembly means to the part holder for translating tilt and rotational motion thereto.

10. A system as set forth in claim 9 above, wherein the gimbal means is tiltable about a predetermined point on the central axis, and wherein the transmission means comprises a number of transmission links disposed circumferentially about the central spindle and including low friction couplings permitting freedom of motion thereat.

11. A mechanism for transferring rotational movement about a central axis and pivotable movement relative to a point on the central axis to a part to be inspected, comprising:
   a central spindle;
   a low friction central pivot ball coupled to a first end of the central spindle;
   part holder means coupled to the central pivot ball and including a low friction socket receiving the central pivot ball; and
   means including a plurality of satellite low friction pivot balls coupled to the part holder at a radius from the central axis and at circumferential positions thereat.

12. The invention as set forth in claim 11 above, further including means engaging the satellite pivot balls for rotating the part holder, and wherein the central spindle, the ball and part holder means include communicating internal conduits for maintaining a part on the part holder means by suction.

13. A system for inspection of a part using radiant energy reflected off the part, comprising:
   a part holder lying in a given plane concentric with a central axis;
   transport means for moving parts to be inspected to and from the part holder;
   means coupled to the part holder for tilting the part holder in either of two directions lying in separated planes that are orthogonally spaced from the central axis; and
   means coupled to the means for tilting for rotating the part holder and the part about the central axis.

14. A system as set forth in claim 13 above, wherein the part to be inspected is a semiconductor wafer, wherein the part holder comprises a vacuum chuck, and wherein the system further comprises means for providing a vacuum acting on the wafer at the vacuum chuck.

15. The invention as set forth in claim 14 above, wherein the system further comprises a dry, low friction ball and socket joint disposed along the central axis and including means for communicating a vacuum to the vacuum chuck, center spindle means including a central conduit coupled to the ball; and control gimbal means coupled to the vacuum chuck for pivoting the vacuum chuck to different pivot positions.

* * * * *